(12) United States Patent
Sweatt et al.

(10) Patent No.: US 7,336,351 B1
(45) Date of Patent: Feb. 26, 2008

(54) LASER REMOTE SENSING OF BACKSCATTERED LIGHT FROM A TARGET SAMPLE

(75) Inventors: William C. Sweatt, Albuquerque, NM (US); John D. Williams, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 83 days.

(21) Appl. No.: 11/348,938

(22) Filed: Feb. 7, 2006

(51) Int. Cl.
*G01J 3/44* (2006.01)
*G01J 3/443* (2006.01)
*G01N 21/64* (2006.01)
*G01N 21/65* (2006.01)
*G01N 21/17* (2006.01)
*G01N 21/39* (2006.01)
*G01N 21/35* (2006.01)

(52) U.S. Cl. .................. 356/301; 356/318; 356/51; 356/342; 356/244

(58) Field of Classification Search .............. 356/301, 356/51, 244, 318, 342
See application file for complete search history.

(56) References Cited

U.S. PATENT DOCUMENTS

| | | | |
|---|---|---|---|
| 6,593,582 B2 * | 7/2003 | Lee et al. ............ | 250/458.1 |
| 6,608,677 B1 * | 8/2003 | Ray et al. ............ | 356/301 |
| 6,781,690 B2 * | 8/2004 | Armstrong et al. .... | 356/301 |
| 7,123,359 B2 * | 10/2006 | Armstrong et al. .... | 356/301 |
| 7,242,469 B2 * | 7/2007 | Wang et al. .......... | 356/301 |
| 2004/0150818 A1 * | 8/2004 | Armstrong et al. .... | 356/301 |
| 2005/0018194 A1 * | 1/2005 | Thirstrup et al. ..... | 356/445 |
| 2005/0207943 A1 * | 9/2005 | Puzey ................. | 422/82.05 |
| 2006/0231771 A1 * | 10/2006 | Lee et al. ............ | 250/458.1 |
| 2006/0255292 A1 * | 11/2006 | Ja .................... | 250/484.2 |

OTHER PUBLICATIONS

F. Yan, "Surface—Enhanced Raman Scattering Detection of Chemical and Biological Agent Simulants," IEEE Sensors Journal, vol. 5, No. 4, Aug. 2005.

P. J. Hargis, Jr., "Multispectral Ultraviolet Fluorescence Lidar for Environmental Monitoring," SPIE vol. 2366, pp. 394-402, Feb. 1995.

(Continued)

*Primary Examiner*—Gregory J. Toatley, Jr.
*Assistant Examiner*—Bryan J Giglio
(74) *Attorney, Agent, or Firm*—Kevin W. Bieg

(57) ABSTRACT

A laser remote sensing apparatus comprises a laser to provide collimated excitation light at a wavelength; a sensing optic, comprising at least one optical element having a front receiving surface to focus the received excitation light onto a back surface comprising a target sample and wherein the target sample emits a return light signal that is recollimated by the front receiving surface; a telescope for collecting the recollimated return light signal from the sensing optic; and a detector for detecting and spectrally resolving the return light signal. The back surface further can comprise a substrate that absorbs the target sample from an environment. For example the substrate can be a SERS substrate comprising a roughened metal surface. The return light signal can be a surface-enhanced Raman signal or laser-induced fluorescence signal. For fluorescence applications, the return signal can be enhanced by about $10^5$, solely due to recollimation of the fluorescence return signal. For SERS applications, the return signal can be enhanced by $10^9$ or more, due both to recollimation and to structuring of the SERS substrate so that the incident laser and Raman scattered fields are in resonance with the surface plasmons of the SERS substrate.

24 Claims, 6 Drawing Sheets

OTHER PUBLICATIONS

R. Joseph Simonson, "Remote Detection of Nitroaromatic Explosives in Soil Using Distributed Sensor Particles," Proc. SPIE, vol. 4394, (2001) 879-889.

C. D. Geddes, "Metal-Enhanced Fluorescence," Journal of Fluorescence, vol. 12, No. 2, Jun. 2002, pp. 121-129.

J. R. Lakowicz, "Radiative Decay Engineering: Biophysical and Biomedical Applications," Analytical Biochemistry, 298, (2001) pp. 1-24.

R. M. Measures, Laser Remote Sensing: Fundamentals and Applications, Wiley—Interscience (1984) 1-79.

G. A. Baker, "Progress in plasmonic engineering of surface-enhanced Raman-scattering substrates toward ultra-trace analysis," Anal Bioannal Chem (2005) 382, 1751-1770.

D. L. Stokes, "Development of an integrated single-fiber SERS sensor," Sensors and Actuators B 69 (2000) 28-36.

J. F. Bertone "A nanoengineered sensor to detect vibrational modes of warfare agents/explosives using surface-enhanced Raman scattering," Proc. Of SPIE vol. 5403, (204) 387-394.

* cited by examiner

LASER REMOTE SENSING OF BACKSCATTERED LIGHT FROM A TARGET SAMPLE

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to laser remote sensing and, in particular, to laser remote sensing based on backscattered Raman or fluorescence light from a target sample.

BACKGROUND OF THE INVENTION

Significant investment has been made in developing optical methods for the remote or stand-off detection of trace chemicals, environmental pollutants, high explosives, and chemical and biological agents. In particular, detection can be achieved by laser remote sensing based on Raman scattering or laser-induced fluorescence from a target sample. Therefore, radiation detected at wavelengths different from that of the laser's output can contain highly specific molecular information that can be used to determine the composition of the target sample.

Raman spectroscopy uses a single frequency of radiation to irradiate a sample and detects the inelastically scattered radiation that is one vibrational unit of energy different from the incident radiation. Raman scattering is strongest when vibrations cause a change in the polarizability of the electron cloud around the molecule. Therefore, the difference in energy between the incident and scattered photons is a characteristic of and provides structural information about the irradiated molecule. Further, due to its narrow spectral lines and unique signatures, Raman spectroscopy enables selective identification of individual analytes in a complex, multicomponent mixture without the need for chemical separations. In addition, the technique requires little or no sample preparation, is nondestructive, and can use water as a solvent (since water is a poor Raman scatterer). The intensity of the scattering is related to the power of the laser used to excite the scattering, the square of the polarizability of the molecule, and the fourth power of the frequency of the exciting laser. Therefore, the most common choice is a visible laser for excitation.

Unfortunately, Raman scattering is an inherently weak process, precluding the possibility of remote trace analysis without some form of enhancement. However, surface-enhanced Raman scattering (SERS) can give an enhancement of up to about $10^6$-$10^7$ in scattering efficiency over normal Raman scattering. Even stronger enhancements, of order $10^{11}$-$10^{13}$, come from sharp features or "hot spots", such as are found in nanostructures. Such extremely large enhancements can produce a total SERS cross-section comparable to that of fluorescence.

In particular, SERS can give molecularly specific information about an adsorbate on a roughened metal surface and can be carried out in a wide range of environments. When the metal surface is irradiated by the incident laser light, conduction electrons in the metal are displaced into an oscillation of frequency equal to the incident light. When spatially confined, for example by a roughened surface, these oscillating electrons, or surface plasmons, produce a secondary electric field that adds to the incident field. The interaction between the sample and the plasmons can occur by either electromagnetic or chemical enhancement. With electromagnetic enhancement, the excitation of the surface plasmon greatly increases the local field of the molecule absorbed on the surface, increasing the polarization around the molecule. Although electromagnetic enhancement does not require direct contact of the molecule with the metal, the dependence on distance is extremely strong. Chemical enhancement involves the formation of a bond between the molecule and the metal surface, enabling charge transfer from the metal surface to the molecule, again increasing the molecular polarizability. Enhancement is maximized when both the incident laser and Raman scattered fields are in resonance with the surface plasmons. Such highly localized surface plasmons are thought to produce very strong fields, or "hot spots", over areas as small as a few nanometers, enabling single-molecule detection. Silver is a particularly good substrate for SERS, although other metals, such as gold and copper, also give good enhancement. Both silver and gold plasmons oscillate at frequencies in the visible region, suitable for use with a visible laser. If the surface metal film is thin (e.g., less than 15 nm), the much larger surface plasmon spans the film and is operative on both sides. Thus, the interaction between the molecule and the plasmon on one side of the film can be detected on the other side. See F. Yan et al., "Surface-Enhanced Raman Scattering Detection of Chemical and Biological Agent Simulants," *IEEE Sensors Journal* 5(4), 665 (2005), which is incorporated by reference.

With laser-induced fluorescence, the laser radiation is matched to a specific electronic transition of the atom or molecule, or fluorophore, which subsequently emits radiation at a lower frequency (i.e., longer wavelength). Typically, a tunable ultraviolet laser source can be used to excite visible fluorescence. Although typically much more efficient than Raman scattering, broadband emission is observed with most molecules. Therefore, laser-induced fluorescence provides less specific molecular information than Raman scattering. However, multispectral analysis algorithms can be used with a database of fluorescence signatures to obtain species concentrations. See P. J. Hargis et al., "Multispectral ultraviolet fluorescence lidar for environmental monitoring," *Proc. of SPIE* 2366, 394 (1995); and R. J. Simonson et al., "Remote Detection of Nitroaromatic Explosives in Soil using Distributed Sensor Particles," *Proc. of SPIE* 4394, 879 (2001); which are incorporated herein by reference.

Surface-enhanced fluorescence (SEF), or metal-enhanced fluorescence, has also been observed for weakly fluorescent substances placed at suitable distances (e.g., 5-20 nm) from metallic surfaces and particles (e.g., metal colloids or islands). Depending upon the distance and geometry, metal surfaces or particles can result in enhancement of fluorescence by factors of $10^3$. This enhancement results from the fluorophore dipole interacting with free electrons in the metal. Proximity to nearby metallic surfaces can also increase the local light field and modify the rate of excitation. See C. D. Geddes and J. R. Lakowicz, "Metal-Enhanced Fluorescence," *J. Fluor.* 12(2), 121 (2002), and J. R. Lakowicz, "Radiative Decay Engineering: Biophysical and Biomedical Applications," *Anal. Biochem.* 298, 1 (2001), which are incorporated herein by reference.

A Light Detection and Ranging (LIDAR) instrument can be used to obtain remote SERS or fluorescence measurement of samples. A LIDAR instrument comprises a laser source for irradiation of the remote sample, a collection telescope for collecting the returned signal from the sample, and a spectrally-resolved photodetector to detect the returned signal. See R. M. Measures, *Laser Remote Sensing: Fundamentals and Applications*, Wiley-Interscience (New York) 1984.

However, in the usual LIDAR system, the backscattered light is nondirectional and the returned signal falls off by an inverse-square dependence with range. Therefore, a need remains for laser remote sensing apparatus wherein the backscattered light is returned to the detector with high efficiency to enable trace analysis of remote chemical or biological samples.

SUMMARY OF THE INVENTION

The present invention is directed to a laser remote sensing apparatus, comprising a laser to provide collimated excitation light at a wavelength; a sensing optic, comprising at least one optical element having a front receiving surface to focus the received excitation light onto a back surface comprising a target sample and wherein the target sample emits a return light signal that is recollimated by the front receiving surface; a telescope for collecting the recollimated return light signal from the sensing optic; and a detector for detecting and spectrally resolving the collected return light signal.

The back surface can further comprise a substrate that absorbs the target sample from an environment. The substrate can be a SERS or SEF substrate. The laser is preferably a monochromatic visible or near-infrared laser or a tunable ultraviolet laser. The optical element can be a simple lens, a ball lens, a two-element lens, or a Schmidt-type system.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
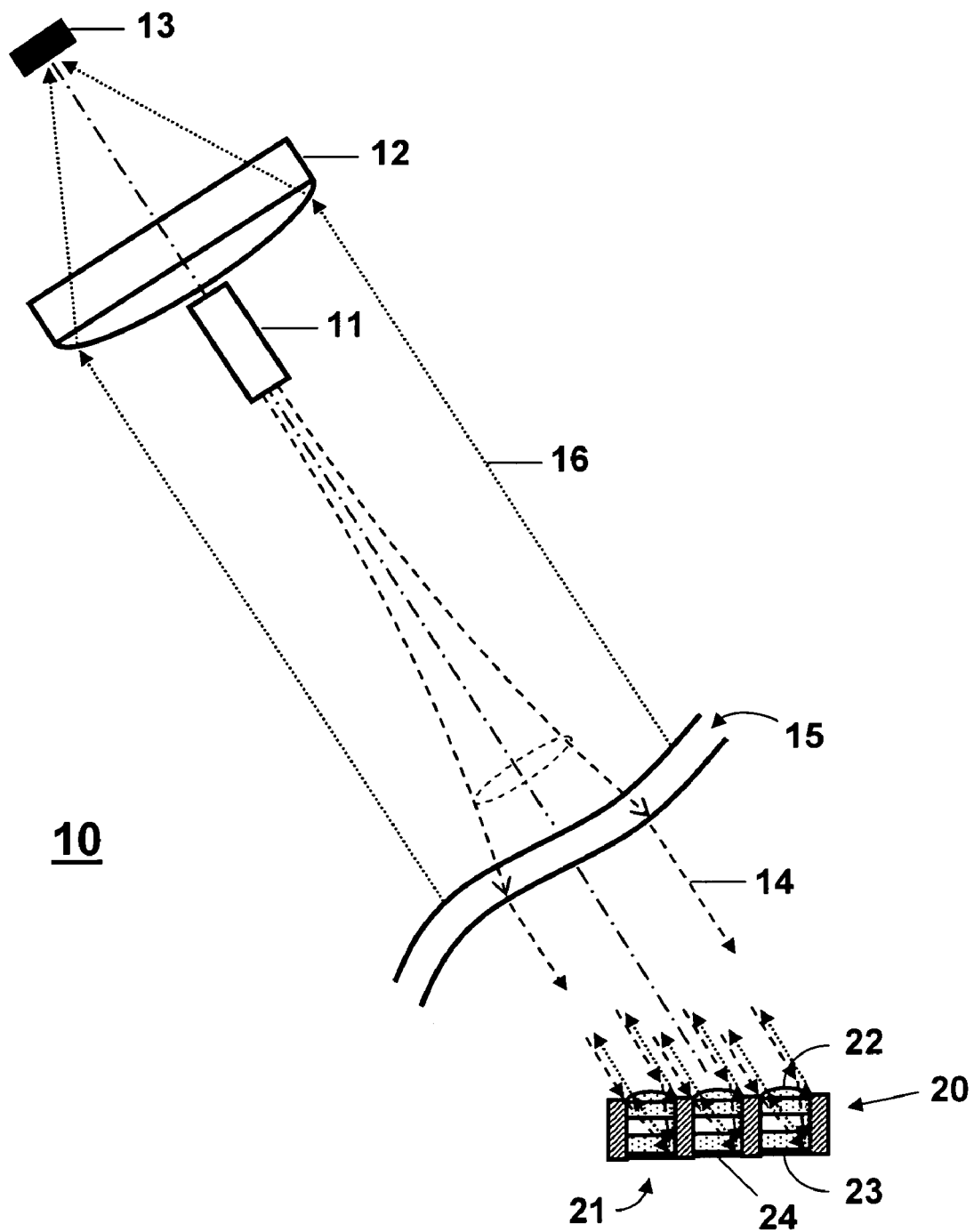
FIG. 1 shows a schematic illustration a laser remote sensing apparatus that can be used to detect backscattered light from a target sample.

In FIG. 1 is shown a schematic illustration of a laser remote sensing apparatus 10, comprising a laser source 11, a sensing optic 20, a collection telescope 12, and a spectrally-resolved detector 13. The apparatus 10 can be used to obtain SERS or fluorescence measurements of molecules that are on or within a depth of focus of the back surface 23 of the distant sensing optic 20.

For SERS measurements, the laser 11 can provide a monochromatic light source that has high power and frequency, and is not absorbed in the propagating atmosphere. Preferably the laser light has a narrow bandwidth and propagates with low divergence. For example, the laser 11 can be a high-power visible or near-infrared laser. For laser-induced fluorescence, the laser can be a monochromatic laser at a known excitation wavelength of a sample molecule. Alternatively, the laser can be a tunable laser that can be tuned over a broad frequency range, to enable excitation of a sample comprising unknown species.

The excitation laser light 14 can be transmitted to the sensing optic 20 coaxially with the detector field of view. The laser 11 can comprise optics that collimate the excitation light 14. However, because of divergence, the diameter of the laser beam 14 grows with distance from the laser 11 as it propagates through the atmosphere 15. Therefore, the sensing optic 20 preferably has an entrance aperture comparable to or larger than the diverged beam diameter. The sensing optic 20 can comprise one or more optical elements 21 that collect the excitation light 14 and focus the collected light onto a back surface 23 of the sensing optic 20. The focused light can produce a backscattered SERS or laser-induced fluorescent signal from a target sample that is on the back surface or within the depth of focus of the incident light. Preferably, the back surface 23 can further comprise a substrate 24 that adsorbs the sample to be detected from the environment and provides a backscattered SERS or fluorescence signal that is related to the adsorbed sample.

The substrate 24 can be a highly enhancing SERS substrate, such as roughened metallic surface on which the molecules to be sensed are adsorbed. Preferably, the SERS substrate should be robust, easy to prepare, give reliable and reproducible results, and provide a stable surface for chemical functionalization. The roughened surface provides the intense localized electric fields that interact with the molecules that adsorb to the metallic surface. Further, because the incident laser beam arrives at the substrate at a known direction, the SERS surface can be structured to maximize the enhancement such that both the incident laser and Raman scattered fields are in resonance with the surface plasmons. Prior experiments with "hot spot" features with nanostructured substrates suggest that the return signal can be enhanced by $10^9$ or more over conventional SERS, due both to recollimation and to proper structuring of the SERS substrate. If the SERS substrate is thin (e.g., less than 15 nm), molecules adsorbed on the backside of the substrate can be detected on the frontside of the substrate. However, since excitation occurs from the backside of the substrate, some attenuation of the SERS emission will occur.

Surface morphologies include roughened surfaces, metal films or discontinuous metal islands deposited on surfaces, colloidal powders, aqueous sols, beads or scaffolds decorated with metal colloids, or structurally inhomogeneous metal surfaces. Alternatively, the metallic surface can be a nanostructured metallic surface comprising posts, metal-coated nanospheres, metal island films, or the like. Noble metals, such as silver, gold, and copper, show particularly strong SERS enhancements. Transition metals are also being increasingly investigated as SERS substrates. See G. A. Baker and D. S. Moore, "Progress in plasmonic engineering of surface-enhanced Raman-scattering substrates toward ultra-trace analysis," *Anal. Bioanal. Chem.* 382, 1751 (2005); D. L. Stokes and T. Vo-Dinh, "Development of an integrated single-fiber SERS sensor", *Sensors and Actuators B*69, 28 (2000); and J. F. Bertone et al., "A nanoengineered sensor to detect vibrational modes of warfare agents/explosives using surface-enhanced Raman scattering," *Proc. of SPIE* 5403, 387 (2004), which are incorporated herein by reference.

Alternatively, the substrate 24 can be a SEF substrate. The SEF substrate can comprise a metallic surface or particles that are spaced a suitable distance from the adsorbed sample by a spacer layer. Further, the particles can be structured to have an elongated spheroid or similar shape whereby the orientation the fluorophore's dipole and the dipole of the metal particle are synergistic.

The backscattered light from the back surface 23 is recollimated by the refractive front surface 22 of the sensing optic 20. The returned light 16 is gathered by the collection telescope 12 that focuses the returned light 16 onto the spectrally resolved detector 13. The collection telescope 12 can be a simple magnifying objective (as shown). Alternatively, other types of collection telescopes can also be used, such as Newtonian or Cassegrainian reflecting telescopes.

The spectrally resolved detector 13 can comprise a spectrometer or optical filter that selects the observation wavelength interval and discriminates against background radiation at other wavelengths. Therefore, the spectrometer can reject laser-reflected radiation, Rayleigh scattered radiation, solar radiation, and other radiation having wavelengths different from that of the returned signal 16. The detector 13 can further comprise a photodetector that can be selected based on spectral response, quantum efficiency, noise, size, and cost. For example, the photodetector can be a photomultiplier or a charge-coupled-device (CCD) detector.

A variety of optical elements 21 can be used, depending on the application. Below are described a simple lens, a high-index sphere, a two-element lens with a flat image plane, and a one-piece Schmidt camera. These optical elements can be characterized by their field of view, F/number, numerical aperture (NA), and spectral range or wavelength band over which the optic can be used. The numerical aperture of the optical element is preferably large to maximize the amount of SERS or fluorescence returned signal collected. Depending on the design, the field of view can be greater than +30°, and perhaps as great as ±60°. The optical elements can be designed, for example, using the ZEMAX® optical design and analysis software (ZEMAX Development Corporation, Bellevue, Wash.).

Figure 2:
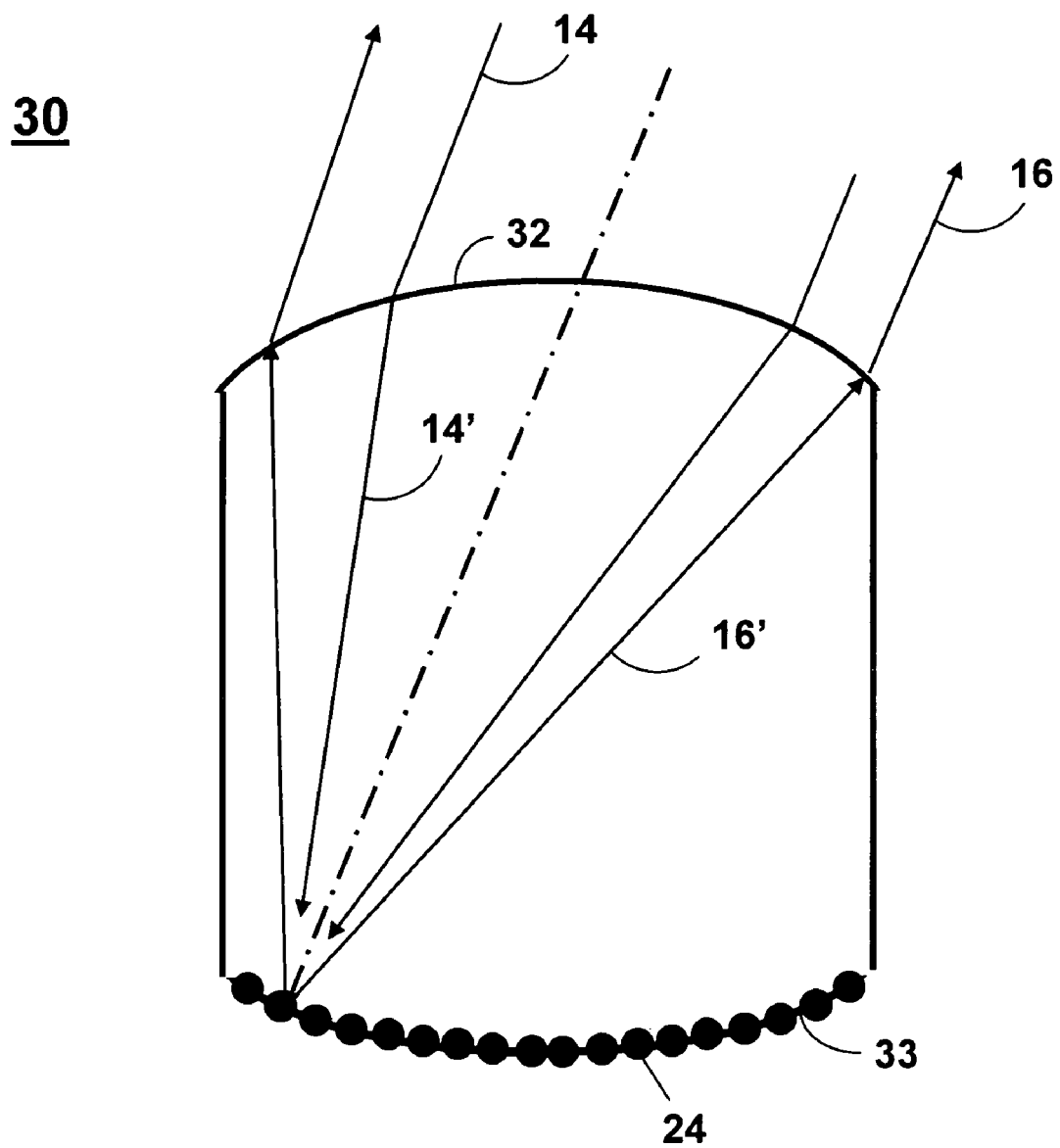
FIG. 2 shows a simple lens that can be an optical sensing element of the sensing optic of the laser remote sensing apparatus.

In FIG. 2 is shown a simple lens 30 that can be an optical element 21 of the sensing optic 20. The simple lens 30 comprises an optical material having a focusing front surface 32 and a curved image plane 33. Parallel rays 14 from the distant laser source 11 having wavelength λ enter the front surface 32. The entering light 14 is redirected by the refractive front surface 32 and the refracted rays 14' come to focus on the curved image plane 33. The refractive front surface 32 can be an aspherical surface to correct for spherical and higher order aberrations. The image plane 33 can be coated with a substrate 24 that adsorbs the sample to be detected from the environment and emits a SERS or fluorescence return signal 16' that is related to the concentration of the adsorbed sample. The return signal rays 16' are recollimated by the refractive front surface 32 and the semi-collimated return signal 16 can be transmitted to the collection telescope 12 coaxially with the excitation light 14. Divergence of the returned signal will be due to the finite lens diameter, size of the emitting spot, and aberrations. With only one surface that can be specified to optimize image quality, the simple lens can only have good image quality over a limited field of view. Therefore, the simple lens 30 is most useful for short range applications where the collecting aperture in the telescope 12 is large and can collect a poorly imaged signal beam.

For purpose of example, consider an F/1 simple lens with a clear aperture of D=0.5-mm and with a return signal at a wavelength of λ=0.5 μm. Assume also that the laser is located kilometers away from the simple lens, so that the excitation rays are parallel. For a system with infinite object distances, the F-number (F/#) and numerical aperture (NA) are related by F/#=1/2NA. Therefore, the collection angle behind the front surface lens will be NA=±0.5 (for F/1). The divergence angle outside the diffraction-limited lens will be approximately 2λ/D=2 mr. Therefore, the increase in return signal irradiance at the receiver, compared to a nondirectional return signal, will be (1-radian/2-mr)$^2$=2.5×10$^5$.

Figure 3:
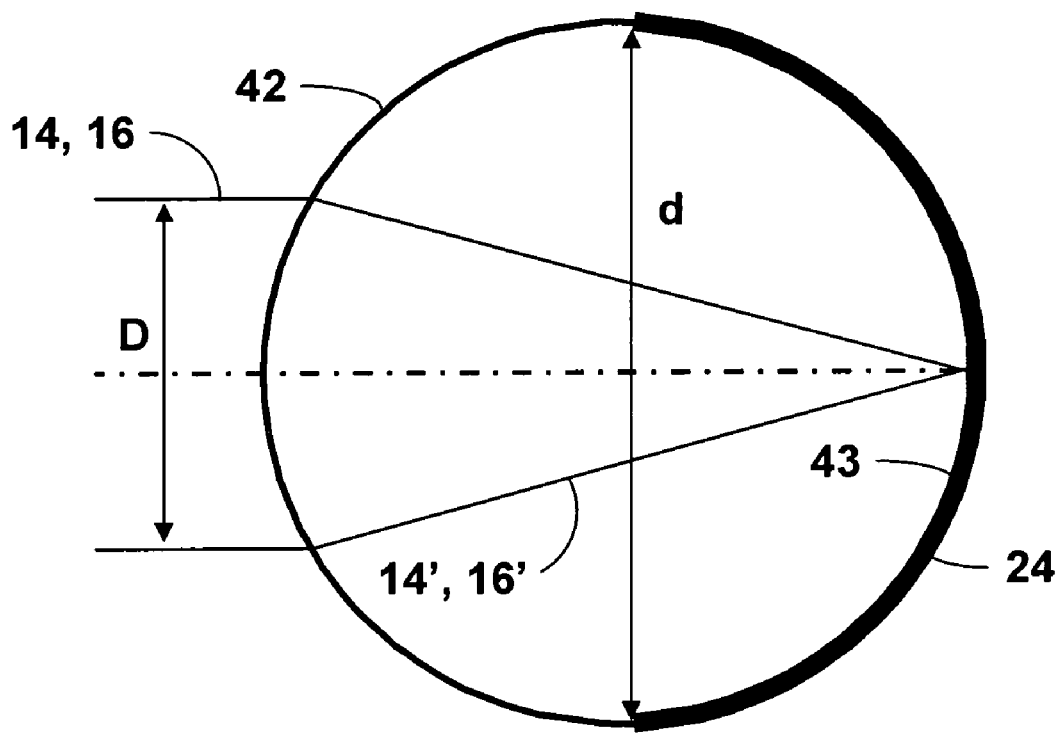
FIG. 3 shows a high-index sphere ("ball lens") that can be an optical sensing element.

In FIG. 3 is shown a high-index sphere ("ball lens") 40 that can be an optical element 21 of the sensing optic 20. Such ball lenses are frequently used to provide short focal lengths for use with collimated light. The power of the ball lens is defined by the sphere diameter d and the index of refraction of the two media before and after the refracting surface 42. For an excitation beam propagating in air, the effective focal length of a ball lens is given by $$f = \frac{nd}{4(n-1)},$$

where n is the index of refraction of the sphere. Therefore, a sphere having an index of refraction of n=2 will focus the incoming excitation beam 14 on the sphere's rear surface 43 and then recollimate the backscattered light 16 generated at the rear surface 43 and direct it back toward the excitation laser 11. The rear surface 43 can be coated with a substrate 24 that adsorbs the sample to be detected from the environment and emits a SERS or fluorescence return signal 16' that is related to the concentration of the adsorbed sample. The ball lens has good imagery for an F/2 beam. The numerical aperture of the ball lens 40 is given by $$NA = \frac{2D(n-1)}{nd},$$

where D is the input diameter of the excitation beam. The high angle of incidence of the outer limiting rays causes these outer rays to refract very strongly. Therefore, the ball lens has some spherical aberration when the NA of the collected cone becomes large. Indeed, spherical aberration increases with the fourth power of the NA. For example, a 1-mm diameter sphere will be diffraction-limited only over a D=0.41-mm diameter central region. However, the field of view of a sphere can approach ±80°. The sphere index must be very close to two for the ball lens to work well, which restricts the glass types. Also, a high-index ball lens will give a Fresnel reflection of about 11% per refraction.

Chromatic aberrations can occur when using refractive optical surfaces, due to chromatic dispersion. In particular, a high-index sphere will show a significant amount of primary axial color, since a single refracting surface is "doing all of the work". The small wavelength shifts as would be seen in a SERS system will not be large enough to cause defocus due to these chromatic aberrations. However, the large wavelength shifts seen in a fluorescence-based system can produce significant axial color and hence diminish the returned signal. Encapsulating the sphere in a plastic or similar low-index material can reduce axial color, however dispersion of the encapsulant can cause "lateral color" for off-normal angles at the plastic/air interface.

Figure 4:
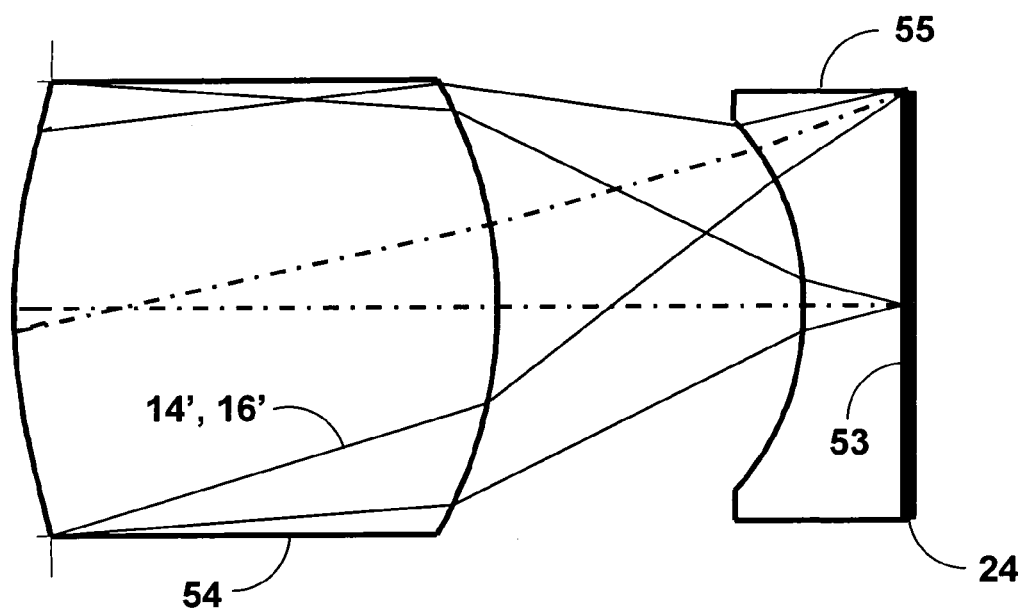
FIG. 4 shows a two-element lens that can be an optical sensing element.

In FIG. 4 is shown a two-element lens 50 that can be an optical element 21 of the sensing optic 20. The two-element lens 50 can create an image on a flat plane 53. A flat image plane 53 may be preferable for patterning a SERS or fluorescence substrate 24 thereon. A first convex lens 54 does the imaging and a second concave lens 55 flattens the field. A two-element lens with a 1-mm entrance pupil can have a 30° field of view in a 2-mm-thick system. The lens 50 can comprise any optical material. However, the two-element lens 50 can be easily assembled with molded plastic parts.

Figure 5:
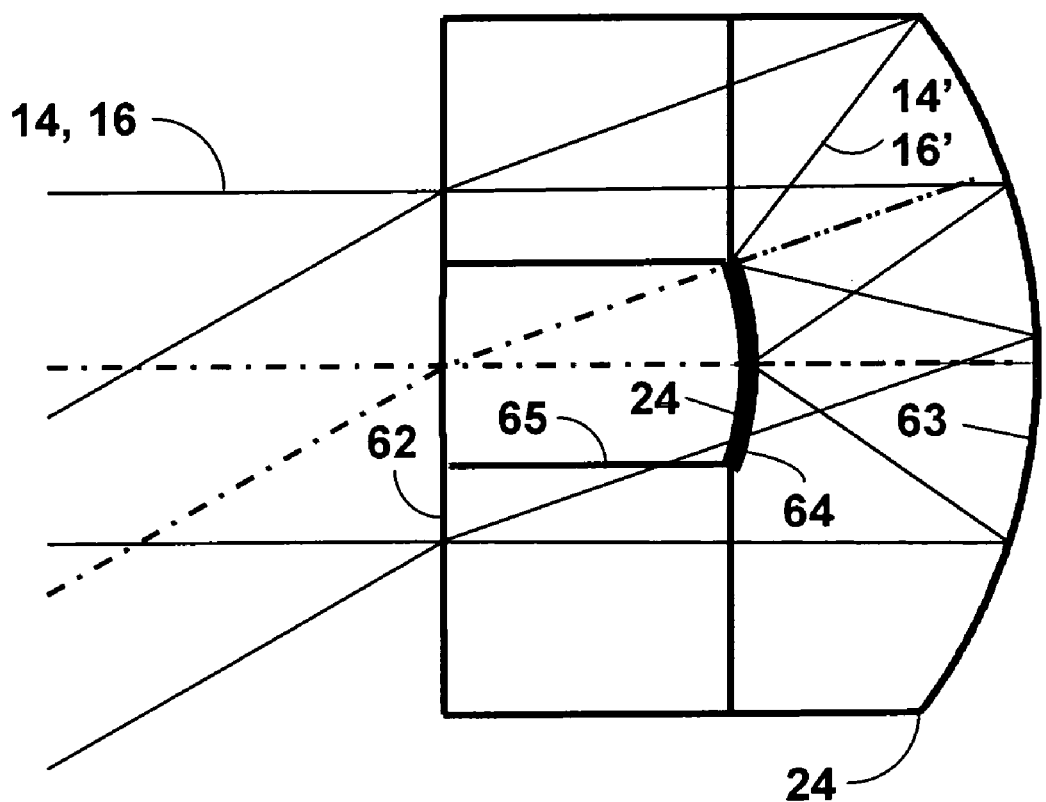
FIG. 5 shows a Schmidt-type system that can be an optical sensing element.

In FIG. 5 is shown a Schmidt-type reflective system 60 that can be an optical element 21 of the sensing optic 20. The Schmidt-type system 60 comprises a spherical mirror 63 with a refracting aspheric corrector surface 62 located at the center of curvature of the mirror 63. The refracting aspheric surface 62 corrects for spherical aberration introduced by the spherical reflecting surface 63. An image is formed on a spherical focal plane 64, with the image radius equal to one-half the mirror radius. The focal plane 64 can be coated with a substrate 24 that adsorbs the sample to be detected from the environment and emits a SERS or fluorescence return signal 16' that is related to the concentration of the adsorbed sample. Nearly all of the focusing is done by the mirror surface 63 so there is almost no axial color, though there will be some lateral color due to the refracting surface 62.

For example, with Schmidt-type reflective system 60 having a pupil that is 1-mm in diameter, the field of view is ±60°. This exemplary system provides diffraction-limited imagery at a 0.55-μm wavelength. The system can be very fast, with NA about 1 and F/# about F/0.5. Therefore, a large fraction of the backscattered light can be captured and recollimated. The central obscuration loses 25% of the input and output beams 14 and 16 on-axis and about 35% off axis. This system can be molded in plastic, with one surface producing the mirror 63 and the other producing both the image plane 64 and the front surface 62, with the image plane 64 located at the bottom of a cylindrical hole 65.

Figure 6:
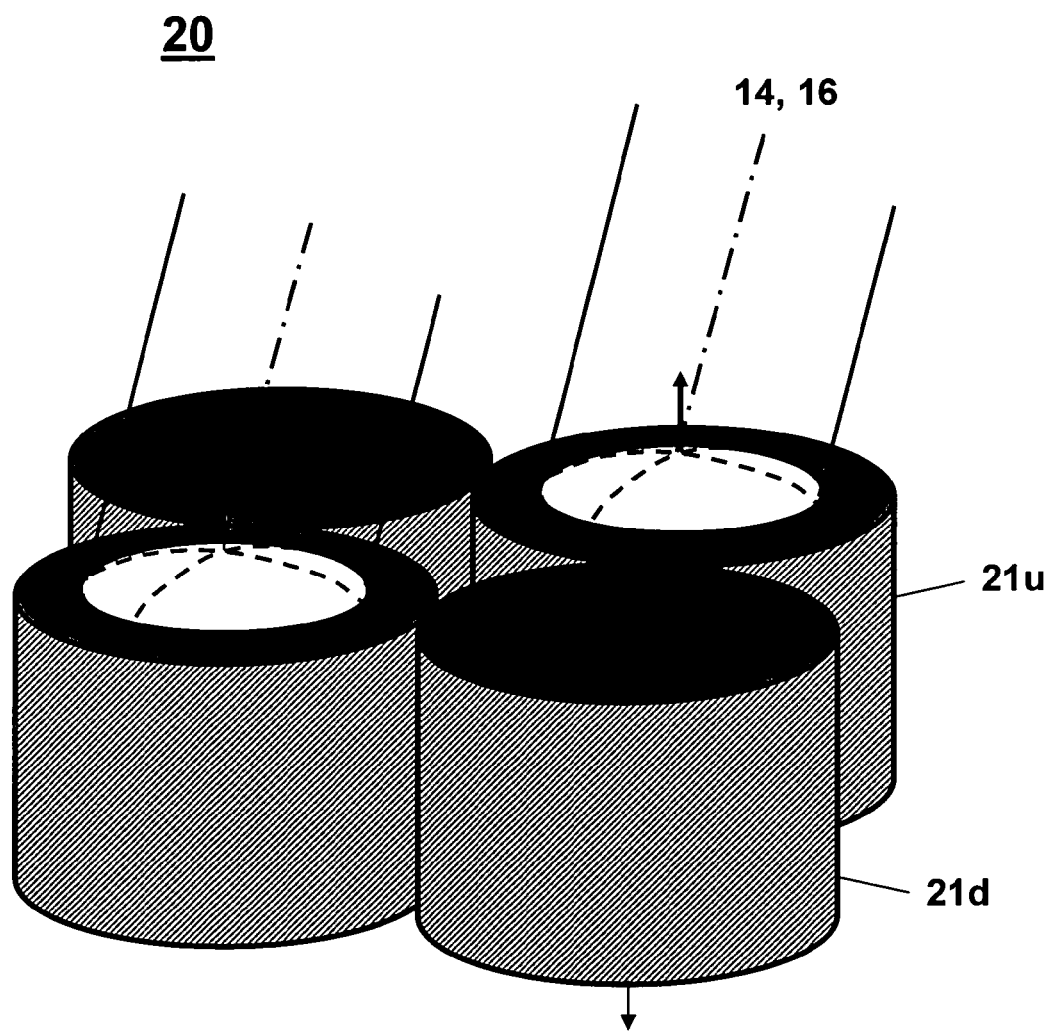
FIG. 6 shows a 2×2 array of optical elements facing different directions.

If the sensing optics 20 are to be dispersed across a landscape, the sensing optic 20 can comprise a plurality of optical elements 21 facing different directions. With a plurality of optical elements 21 facing different directions, the telescope 12 can be within the field of view of at least one, or more, of the optical elements 21. For example, a cubic sensing optic has six surfaces, any one of which could be facing up. In FIG. 6 is shown a 2×2 array of optical elements, wherein two elements 21u are facing up and two elements 21d are facing down. Therefore, with such an array, two of the optical elements will "lie" facing toward the sky.

The present invention has been described as a laser remote sensor of backscattered Raman or fluorescent light. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A laser remote sensing apparatus, comprising:
    a laser to provide collimated excitation light at a wavelength;
    a sensing optic, comprising at least one optical element having a front receiving surface to focus the received excitation light onto a back surface comprising a target sample and wherein the target sample emits a return light signal that is recollimated by the front receiving surface and wherein the optical element comprises a two-element lens comprising a first convex lens providing the front receiving surface and a second concave lens having a flat image plane providing the back surface;
    a telescope for collecting the recollimated return light signal from the sensing optic; and
    a detector for detecting and spectrally resolving the collected return light signal.

2. The apparatus of claim 1, wherein the return light signal comprises Raman scattered light from the target sample.

3. The apparatus of claim 1, wherein the return light signal comprises fluorescent light from the target sample.

4. The apparatus of claim 1, wherein the back surface further comprises a substrate that absorbs the target sample from an environment.

5. The apparatus of claim 4, wherein the substrate comprises a SERS substrate.

6. The apparatus of claim 5, wherein the SERS substrate is structured so that both the excitation light and Raman scattered fields are in resonance with the surface plasmons of the substrate.

7. The apparatus of claim 6, wherein the SERS substrate comprises silver, gold, or copper.

8. The apparatus of claim 6, wherein the excitation laser light and Raman scattered fields are in resonance with the surface plasmons of the SERS substrate.

9. The apparatus of claim 1, wherein the substrate comprises a SEF substrate.

10. The apparatus of claim 1, wherein the laser comprises a monochromatic visible or near-infrared laser.

11. The apparatus of claim 1, wherein the laser comprises a tunable ultraviolet laser.

12. The apparatus of claim 1, wherein the field of view of the detector is coaxial with the excitation light.

13. A laser remote sensing apparatus, comprising:
    a laser to provide collimated excitation light at a wavelength;
    a sensing optic, comprising at least one optical element having a front receiving surface to focus the received excitation light onto a back surface comprising a target sample and wherein the target sample emits a return light signal that is recollimated by the front receiving surface and wherein the optical element comprises a Schmidt-type reflective system;
    a telescope for collecting the recollimated return light signal from the sensing optic; and
    a detector for detecting and spectrally resolving the collected return light signal.

14. The apparatus of claim 13, wherein the return light signal comprises Raman scattered light from the target sample.

15. The apparatus of claim 13, wherein the return light signal comprises fluorescent light from the target sample.

16. The apparatus of claim 13, wherein the back surface further comprises a substrate that absorbs the target sample from an environment.

17. The apparatus of claim 16, wherein the substrate comprises a SERS substrate.

18. The apparatus of claim 17, wherein the SERS substrate is structured so that both the excitation light and Raman scattered fields are in resonance with the surface plasmons of the substrate.

19. The apparatus of claim 18, wherein the SERS substrate comprises silver, gold, or copper.

20. The apparatus of claim 18, wherein the excitation laser light and Raman scattered fields are in resonance with the surface plasmons of the SERS substrate.

21. The apparatus of claim 13, wherein the substrate comprises a SEF substrate.

22. The apparatus of claim 13, wherein the laser comprises a monochromatic visible or near-infrared laser.

23. The apparatus of claim 13, wherein the laser comprises a tunable ultraviolet laser.

24. The apparatus of claim 13, wherein the field of view of the detector is coaxial with the excitation light.

* * * * *